United States Patent [19]

Sogli et al.

[11] Patent Number: 5,945,414

[45] Date of Patent: Aug. 31, 1999

[54] PROCESS FOR THE PREPARATION OF NEW INTERMEDIATES USEFUL IN THE SYNTHESIS OF CEPHALOSPORINS

[75] Inventors: Loris Sogli, Novara; Daniele Terrassan, Concorezzo; Ermanno Bernasconi, Varesino, all of Italy; Francisco Salto, Madrid, Spain

[73] Assignee: Antibioticos S.p.A., Milan, Italy

[21] Appl. No.: 08/982,351

[22] Filed: Dec. 2, 1997

[30] Foreign Application Priority Data

Dec. 3, 1996 [IT] Italy .................................. MI96A2533

[51] Int. Cl.$^6$ ...................... A61K 31/545; C07D 501/36
[52] U.S. Cl. ........................ 514/203; 514/204; 514/205; 540/224; 540/225; 540/226
[58] Field of Search .................... 540/224, 225, 540/226; 514/203, 204, 205

[56] References Cited

U.S. PATENT DOCUMENTS

| 3,516,997 | 6/1970 | Takano et al. ....................... 260/243 C |
| 5,387,679 | 2/1995 | Sogli et al. ............................. 540/226 |

FOREIGN PATENT DOCUMENTS

| 45717 | 2/1982 | European Pat. Off. . |
| 2 133 927 | 12/1972 | France . |
| 2 258 448 | 8/1975 | France . |
| 1 939 341 | 2/1970 | Germany . |
| 56-53688 | 5/1981 | Japan . |
| WO 93/02085 | 2/1993 | WIPO . |

OTHER PUBLICATIONS

Translation of JP 56–53688, 1981.

Chemical Abstracts, vol. 85, No. 11, 78140v, Sep. 13, 1976, for JP 75–157 389, Dec. 19, 1975.

Chemical Abstracts, vol. 90, No. 11, 87489w, Mar. 12, 1979, for JP 78–112 891, Oct. 2, 1978.

Chemical Abstracts, vol. 85, No. 15, 106611r 7, Apr. 11, 1977, for JP 76–88 694, Aug. 3, 1976.

Chemical Abstracts, vol. 85, No. 9, 63080b, Aug. 30, 1976, for JP 76–44 695, Apr. 16, 1976.

*Primary Examiner*—Mark L Berch
*Attorney, Agent, or Firm*—Oblon, Spivak, McClelland, Maier & Neustadt, P.C.

[57] ABSTRACT

Cefazolin, cefazedone, cefoperazone, cefamandole, cefatrizine or ceftriaxone is prepared by reacting glutaryl 7-ACA of the formula:

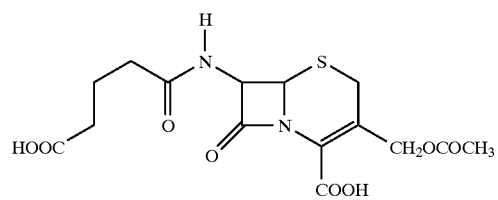

with a compound of formula (II):

R—SH  (II)

wherein R is 5-methyl-1,3,4-thiadiazol-2-yl, 1H-1,2,3-triazol-4-yl, 1-methyl-tetrazol-5-yl or 1,2,5,6-tetrahydro-2-methyl-5,6-dioxo-1,2,4-triazin-3-yl group, and $R^1$ and $R^2$ are both hydrogen and the other is an acyl group, in an aqueous solution in an amount of 3–5 mols per mol of glutaryl 7-ACA to about 90° C. and for a time from about 2 to about 10 hours; optionally recovering the excess of the compound of formula (II), thereby preparing a compound of formula (III) in an aqueous solution:

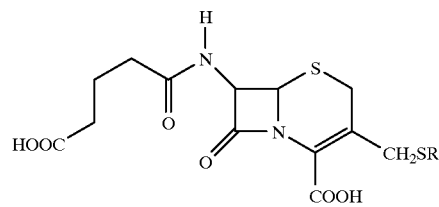

wherein R is as above defined and optionally deacylating said compound of formula (III); and
converting the resulting compound of formula (I)

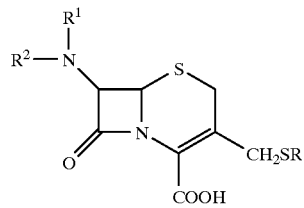

wherein R, $R^1$ and $R^2$ are as defined above in the presence of a non-chlorinated solvent into one of said cephalosporins.

4 Claims, No Drawings

PROCESS FOR THE PREPARATION OF NEW INTERMEDIATES USEFUL IN THE SYNTHESIS OF CEPHALOSPORINS

The present invention relates to a process for the preparation of new intermediates useful in the synthesis of cephalosporins.

Particularly, the present invention relates to a process for the synthesis of cephalosporin intermediates useful for the production of important cephalosporins, such as cefazolin, cefazedone, cefperazone, cefamandole, cefatrizine, cefatriaxone which are known antibacterial agents.

As to the above mentioned cephalosporins, the most common method of synthesis is the one which goes through the isolation of the sodium salt of the cephalosporin C, the chemical transformation of the latter into 7-aminocephalosporanic acid (herebelow indicated as 7-ACA) which is purified and isolated to be then converted into its derivative, suitably substituted at position 3 (for instance, in the case of cefazolin, the 3-thiadiazolyl-derivative, (herebelow indicated as 3TD, is obtained). The derivative substituted at position 3 is obtained by reacting 7-ACA with the corresponding thiol, or a derivative thereof, in an aqueous or anhydrous medium.

The reaction in an aqueous medium gives lower yields (about 65%) and intermediates substituted in 3 having a lower quality (having a titre of 80–85% and a brown colour), even if they have the advantage to give a waste refluent easily obtainable. A further disadvantage is the need to isolate the intermediate products.

The reaction in the anhydrous environment, disclosed in U.S. Pat. No. 4,317,907 and in WO 93/02085 for the production of cefazolin, uses $BF_3$ or the derivatives thereof in an organic solvent and allows to obtain yields equal to about 85% and 3TD having a higher quality (having a titre equal to about 90% and a white colour). Yet the process shows the problem of the use of a toxic gas such as $BF_3$ and the waste refluent which contains fluoborates.

The choice of the most advantageous method is therefore linked to the possibility to treat the refluent containing borides and fluoborides and to handle toxic gases.

The acid cefazolin is then obtained by acylating, with tetrazolyl acetic acid, the 3TD in an organic solvent; the solvent noted as preferred is, usually, a chlorinated solvent such as methylene chloride, the use of which entails however the evaluation of the ecologic impact.

An alternative synthesis (U.S. Pat. No. 3,516,997) is represented by the use of a solution of cephalosporin C, the obtainment of the sodium salt thereof, which is isolated, then of the 3-thiadiazolyl derivative thereof, isolated and used to obtain 3TD, then isolated and from which the acid cefazolin is obtained; such method results however characterised by low cycle overall yields and by difficulties in isolating the intermediates.

A further method to obtain cefazolin is to use 7-ACA obtained enzymatically (WO 93/02085). The carrying out of such process simplifies the production cycle avoiding the isolation of the cephalosporin C and carrying to cycle overall yields higher than the ones obtained carrying out the method disclosed in U.S. Pat. No. 3,516,997.

A step which is common to the processes for the preparation of cefazolin above discussed is that to carry out the acylation of dried 3TD in the presence of chlorinated solvents (usually methylene chloride); the traces of such solvents result however undesirable in the finished product.

A new process has now been found for the preparation of a compound of formula I:

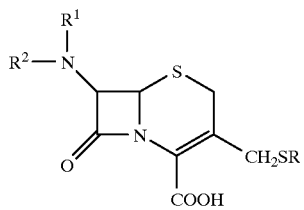

wherein R is a heterocyclic group which contains at least a nitrogen atom with or without a sulphur or oxygen atom and $R^1$ and $R^2$ are both hydrogen atoms or one of them is a hydrogen atom and the other is an acyl group;

the process comprising the reaction of glutaryl 7-ACA in an aqueous solution

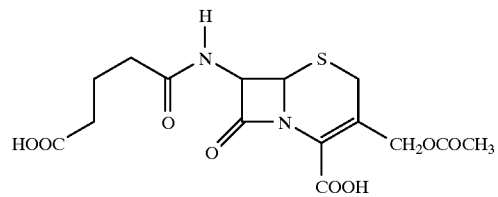

with a compound of formula II:

$$R\text{—}SH \qquad\qquad II$$

wherein R is as above defined, in an amount comprised between 3 and 5 mol/mole of glutaryl 7-ACA;

optionally recovering the excess of the compound of formula II, obtaining a compound of the following formula III in an aqueous solution:

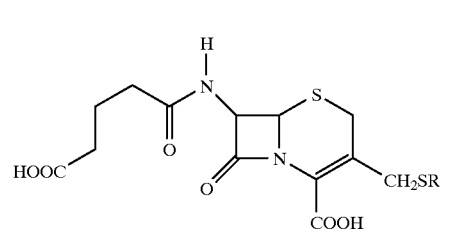

wherein R is as above defined;

deacylating the resulting compound of formula III.

Particularly, the deacylation of the compound of formula III can be advantageously carried out enzymatically, separating the glutaryl 7-ACA acylase enzyme, optionally reusable.

The resulting compound of formula I is then recovered according to known methods.

Particularly, R is a thiadiazolyl, a triazolyl, a tetrazolyl and a tetrahydrotriazinyl, substituted or not substituted and, preferably, R is a 5-methyl-1,3,4-thiadiazol-2-yl, a 1H-1,2,3-triazol-4-yl, a 1-methyl-tetrazol-5-yl, a 1,2,5,6-tetrahydro-2-methyl-5,6-dioxo-1,2,4-triazin-3-yl.

The present invention further discloses a new compound, the 7-aminoglutaryl-3-[(2,5-dihydro-6-hydroxy-2-methyl-5-oxo-1,2,4-triazin-3-yl)-thiomethyl]-cephalosporanic acid:

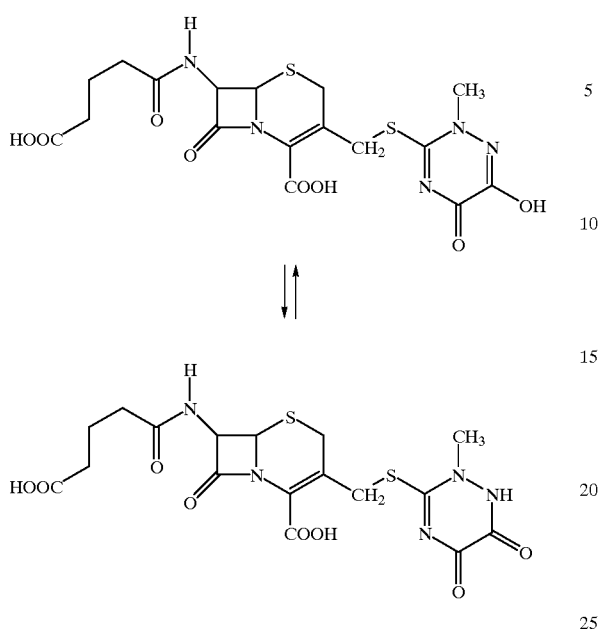

The process of the invention is carried out in an aqueous solution, at a temperature from about 20° C. to about 90° C., preferably from about 40° C. to about 70° C., for a time from about 2 to about 10 hours.

The process of the invention further can be advantageously used for the preparation of some important cephalosporins, such as cefazolin, cefazedone, cefperazone, cefamandole, cefatrizine and cefatriaxone, which can be obtained by converting the compounds of formula I, according to known techniques, as above illustrated.

Further, the present invention comprises a process for the preparation of a pharmaceutical composition which comprises the preparation of said cephalosporins, by the process just described, and the formulation thereof with a pharmaceutically acceptable vehicle.

According to the process of the present invention, in the case of cefazolin, the aqueous solution of the glutaryl 7-ACA, coming from the first step of bioconversion of solubilised cephalosporin C, is reacted under heat (70° C.) with methylmercaptothiadiazol (herebelow noted as MMTD) to obtain the glutaryl 3TD intermediate, still solubilized.

Nucleophilic substitution at position 3, in an aqueous medium, conducted by known techniques, is characterised by a substantial degradation of the beta-lactamic ring due to the combined effect of temperature and of relatively long reaction times (1–2 hours).

It has been surprisingly found that, carrying out the process of the invention, very little degradation of the β-lactam ring occurs.

The deacylation is carried out by enzymatically cutting the side chain of glutaryl 3TD in aqueous solution, using the same technique described in WO 95/35020 relating to the second step of conversion of the glutaryl 7-ACA in 7-ACA.

The process for obtaining cefazolin just described can be illustrated by the following reaction scheme:

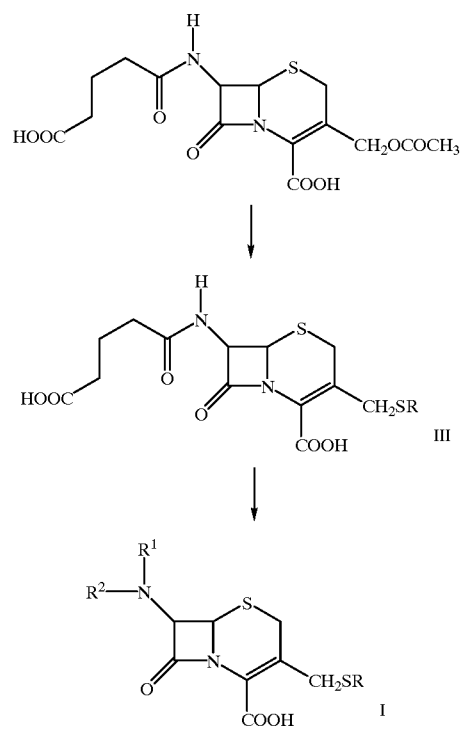

wherein R is as above defined and $R^1=R^2=H$.

The process of the invention is new and permits percentage increases of the molar yield in 3TD of about 10 in comparison with the above discussed methods.

Further advantages, in comparison with the known processes, include avoiding the isolation of 7-ACA, in the possibility of obtaining 3TD having a better quality (titre and colour; the colour being determined on the 1% solution in 2% $NaHCO_3$, absorption at 420 nm; 1 cm cell) and in the ability to arrive till the obtainment of 3TD operating in an aqueous solution.

The elimination of the use of the solvents entails advantages of ecologic and environmental nature, besides to an obvious economic saving.

Besides to representing a new and advantageous synthesis, in aqueous phase, of the compounds of formula I, the process of the invention allows also the elimination of chlorinated solvents in the acylation step of the compounds of formula I to obtain the final cephalosporins (for instance, the wet 3TD obtained according to the process of the invention is acylated in the presence of non-chlorinated solvents such as acetone, dimethylcarbonate, etc.)

The following examples are meant to illustrate the invention with a non limitative purpose.

EXAMPLE 1

Synthesis of Glutaryl 3TD 2500 cc of a solution of Glutaryl 7-ACA were charged in a 3 liter flask (concentration 25.4 mg/cc, equal to 63.5 activity grams). 73.2 g of MMTD were added at the same time and heat was applied till 70° C. in 10 minutes. During the heating 15 g of sodium carbonate were added by portions till a pH of 5.6 was reached.

The temperature was maintained at 70° C. for 120 minutes controlling the reaction kinetics. The following data were obtained:

| Time (minutes) | Concentration (mg/cc) | |
| --- | --- | --- |
| | Glutaryl 7-ACA | Glutaryl 3TD |
| 0 | 22.8 | 1.5 |
| 90 | 2.8 | 20.5 |
| 120 | 1.6 | 21.0 |

After 120', with a residual concentration of glutaryl 7-ACA lower than 2 mg/cc, the reaction was considered finished.

Cooling to 20–25° C., where the crystallisation of the excess of MMTD begins, was applied. The pH was adjusted to 5.2 with concentrated sulphuric acid, letting under slow stirring for 60' for the completion of the crystallisation. The unreacted MMTD was filtered and dried at 35° C. under vacuum. 45.8 g of recovered MMTD were obtained, having a titre of 99%.

The filtered solution containing: Glutaryl 7-ACA 1.6 mg/cc, MMTD 2.8 mg/cc e Glutaryl 3TD 21.0 mg/cc, was carried to the following step of bioconversion to 3TD.

EXAMPLE 2

Synthesis of 3TD

The solution of glutaryl 3TD (2600 cc having a titre of 21.0 mg/cc equal to 54.6 activity grams) was split in three equal portions each of 866 cc.

The enzymatic deacylation was carried out in 3 cycles using the Glutaryl 7-ACA acylase enzyme supported on DIAION HPA 25 resin (produced by Mitsubishi Kasei Corp.) coming from the second step of the bioconversion cycle of Cephalosporin C into 7-ACA).

$1^{st}$ cycle

This first cycle serves for the conditioning of the enzyme.

866 cc of the solution of Glutaryl 3TD and, at the same time, 86.5 g of supported enzyme (titre 43 U/g of wet matrix equal to about 200 U/g of Glutaryl 3TD) were charged. The temperature was maintained at 20° C., adjusting the pH to 8.0 with 4% ammonia for the first 30' and to 8.3 for the next 30', controlling the reaction kinetics:

| Time (minutes) | pH | Concentration (mg/cc) | |
| --- | --- | --- | --- |
| | | Glutaryl 3TD | 3TD |
| 30 | 8.0 | 3.5 | 11,5 |
| 60 | 8.3 | 0.6 | 12,0 |

The mixture was left separating and the solution was siphoned separating it from the wet enzyme.

$2^{nd}$ cycle

The second 866 cc fraction of the Glutaryl 3TD solution was added to the wet enzyme. The temperature of 20° C. was maintained and the pH was adjusted with a 4% ammonia solution to 8.0 for the first 30' and to 8.3 for the next 30'. The reaction kinetics was controlled.

| Time (minutes) | pH | Concentration (mg/cc) | |
| --- | --- | --- | --- |
| | | Glutaryl 3TD | 3TD |
| 30 | 8.0 | 3.8 | 12.4 |
| 60 | 8.3 | 0.8 | 14.5 |

The solution was separated from the wet enzyme. The solution was adjusted to a pH of 5.2 by concentrated sulphuric acid at the temperature of 10° C. and then crystallization occurred with slow stirring. The wet enzyme was passed to the next cycle.

$3^{rd}$ cycle

The third 866 cc aliquot of the Glutaryl 3TD solution was added to the wet enzyme following the same procedure as above illustrated for the $1^{st}$ and the $2^{nd}$ cycle. Kinetic control gave the following indications:

| Time (minutes) | pH | Concentration (mg/cc) | |
| --- | --- | --- | --- |
| | | Glutaryl 3TD | 3TD |
| 30 | 8.0 | 3.6 | 12.7 |
| 60 | 8.3 | 0.7 | 14.6 |

The solution of the wet enzyme, which can be reused, was separated. The 3TD solution was added to the aqueous suspension of 3TD coming from the treatment of the reaction product of the $2^{nd}$ cycle, the pH was adjusted to 5.2 by concentrated sulphuric acid while the temperature was maintained at 10° C. Under slow stirring, crystallization occurred in 60'. Filtering and washing with 400 cc of water and 250 cc of acetone was carried out. Drying at 35° C. under vacuum was carried out.

27.2 g of 3TD having a titre of 93.0% (HPLC purity 96%, colour 95) were obtained. The 3TD amount in the mother liquours was equal to 0.6 g (2370 cc having a concentration of 0.25 mg/cc).

The yield from the starting Glutaryl 7-ACA (63.5 activity grams equal to 0.16434 mol) to 3TD (27.2 g referring to two cycles correspond to a total of 40.8), having a titre of 93% (the activity grams were 37.944, which correspond to 0.11014 mol), was equal to 67%.

$^{1}$H-NMR (DMSO/DCl) (δ ppm): 2.71 (s, 3H, —CH$_3$); 3.78 (broad s, 2H, —CH$_2$—); 4.31–4.60 (Abq, J=13.3 Hz, 2H, —CH$_2$—); 5.14 (d, J=4.9 Hz, 1H, C-6); 5.24 (d, J=4.9 Hz, 1H, C-7).

EXAMPLE 3

Synthesis of Glutaryl 3TD 566 kg of a Glutaryl 7-ACA solution (density=1019; concentration=32.1 mg/cc equal to 17.8 activity Kg) were charged in a 1500 liters reactor. 21.0 Kg of MMTD were added at the same time and the contents were heated at 70° C. for 70'.

3.1 Kg of Na$_2$CO$_3$ were added during the heating to maintain a pH of 5.7.

The mass was cooled at 25° C. in 75' after a synthesis of 90'.

The reaction kinetics was controlled by a HPLC analysis and the following data were obtained:

| | Concentration (mg/cc) | |
|---|---|---|
| Time (minutes) | Glutaryl 7-ACA | Glutaryl 3TD |
| 30 | 7.5 | 23.9 |
| 60 | 2.9 | 27.1 |
| 90 | 1.2 | 28.0 |
| 165 | 0.9 | 28.1 |

The pH was adjusted to 5.2 by 40% $H_2SO_4$ to crystallise the excess MMTD and, after 75', filtering and washing of the panel with 70 liters of water was carried out.

16.2 Kg of wet recovered MMTD (equivalent to 12.0 Kg of dry product)and 648 Kg of a Glutaryl 3TD solution (density=1.028; concentration 25.0 mg/cc) were obtained.

EXAMPLE 4

Synthesis of 3TD

The Glutaril 3TD solution was subdivided into three fractions, each of 216 kg.

The transformation into 3TD occurred by an enzymatic deacylation which was carried out in three cycles, using the Glutaryl 7-ACA acylase enzyme supported on DIAION HPA 25 resin (produced by Mitsubishi Kasei Corp.)

$1^{st}$ cycle

This first cycle serves for the conditioning of the enzyme.

216 kg of the solution of Glutaryl 3TD and 21 kg of the enzyme (titre 50 U/g of wet matrix equal to about 200 U/g of Glutaryl 3TD) were charged in a 350 liter reactor.

The pH of 8.0, at the temperature of 20° C., was maintained with 16 liters of 4% ammonia for 30' and to 8.3 with 2 liters of 4% ammonia for other 30'.

The rection kinetics gave the following results:

| | | Concentration (mg/cc) | |
|---|---|---|---|
| Time (minutes) | pH | Glutaryl 3TD | 3TD |
| 30 | 8.0 | 2.0 | 13.6 |
| 60 | 8.3 | 0.6 | 13.9 |

At the end of the synthesis, the enzyme which is re-charged in the bioconversion reactor, to which 216 kg of a solution of Glutaryl 3TD had been transferred for the $2^{nd}$ cycle, was filtered on a buchner.

The 3TD solution was placed in a 500 liter reactor and adjusted to a pH=5.2 at 20° C. by 3.5 liters of 40% $H_2SO_4$ for the crystallisation of the product.

After 60', the 3TD, first washed with 60 liters of water and then with 35 liters of acetone, was centrifuged.

3.42 kg of 3TD (titre 94.5%, purity 95.2%, K.F. 0.9%) were obtained drying under vacuum at 35° C.

The content in the mother liquours was 83 g (345 liters having a concentration of 0.24 mg/cc).

$2^{nd}$ and $3^{rd}$ cycles.

Also the second and then the third aliquot of the Glutaryl 3TD solution were converted into 3TD following the working procedures illustrated for the $1^{st}$ cycle.

At the end of the $3^{rd}$ cycle the filtered enzyme can be used in other cycles whereas the solution is added to the 3TD suspension coming from the $2^{nd}$ cycle, the pH being adjusted to 5.2 by 40% sulphuric acid and crystallization occurred with slow stirring.

After 60', centrifuging and washing with 120 liters of water and 70 liters of acetone was carried out.

7.86 kg of 3TD (titre 90.4%, purity 94.2%, K.F. 1.0%) were obtained drying under vacuum at 35° C. The content in the mother liquours was 247 g (650 liters having a concentration of 0.38 mg/cc).

The molar yield fom the starting Glutaryl 7-ACA (17.8 KA equal to 46.06 mol) to 3TD (10.06 KA equal to 30.95 mol) was equal to 67.2%.

$^1$H-NMR (DMSO/DCl) (δ ppm): 2.71 (s, 3H, —$CH_3$); 3.78 (broad s, 2H, —$CH_2$—); 4.31–4.60 (Abq, J=13.3 Hz, 2H, —$CH_2$—); 5.14 (d, J=4.9 Hz, 1H, C-6); 5.24 (d, J=4.9 Hz, 1H, C-7).

EXAMPLE 5

Synthesis of Cefazolin (Acylation of Wet 3TD in the Absence of Chlorinated Solvent)

100 cc of acetone and 21.6 g of tetrazolylacetic acid were charged in a 250 cc flask. The pH was adjusted to 7.9, at the temperature of 0° C., by 23.8 cc of triethylamine then the temperature was raised to 18–20° C. and 20.2 cc of pivaloyl chloride were added.

To complete the synthesis of the mixed anhydride, the mixture was stirred at the same temperature for one hour.

24 cc of acetone and 88.6 g of wet 3TD (titre=38.3 equal to 33.9 activity grams, $H_2O$ content=54.2%) were charged, at the same time, in a 1000 cc flask.

The temperature was brought to −12° C. and 26.4 cc of triethylamine were charged.

To complete the dissolution of 3TD, the mixture was left under stirring at the same temperature for one hour and the mixed anhydride, previously prepared in the 250 cc flask, was charged, still at −12° C., in 30'.

The reaction was completed in 45' at −12° C.

The following data can be read from the kinetic controls:

| | Concentration (mg/cc) | |
|---|---|---|
| Time (minutes) | acid Cefazolin | 3 TD |
| 15 | 157.7 | 1.4 |
| 45 | 159.5 | 1.2 |

Once the acylation step was completed, hydrolysing with 200 cc of water was carried out. The pH was adjusted to 5 by glacial acetic acid, after 30' at 5° C., and filtering on a dicalite panel was carried out.

The resulting solution was decolourized with alumina and brought to pH=1.5 by 18% HCl at 15° C. for the crystallisation of the raw acid cefazolin.

The filtered product was then purified with a method which entails first its precipitation under the form of the sodium salt thereof and then its conversion into the final acid form.

35.0 g of acid cefazolin (titre 99.8% on a dry basis, purity=99.7%, K.F. 0.5%; colour=80) were obtained (a 2 g solution in 8 cc of a 4.6% $NaHCO_3$ solution, absorption at 420 nm; 1 cm cell).

EXAMPLE 6

Synthesis of Cefazolin from wet 3TD 144 cc of dimethylcarbonate and 21.6 g of tetrazolylacetic acid were charged in a 500 cc flask. Cooling at 5° C. and bringing to pH=7.9 with 23.8 cc of triethylamine were carried out, then 20.2 g of pivaloyl chloride were added maintaining the same temperature.

The synthesis of the mixed anhydride was completed in one hour at 5° C.

58 cc of dimethylcarbonate, 24 cc of isopropyl alcohol and 88.6 g of wet 3TD (titre=38.3% equal to 33.9 activity grams, $H_2O$ content=54.2%) were charged in a 1000 cc flask in concomitance with the previous reaction. Cooling to 5° C. and adding 26.4 cc of triethylamine was carried out.

The mixture was kept under stirring for one hour at the same temperature then, still at 5° C., the mixed anhydride previously prepared was charged in 30'.

After 45' at 5° C., hydrolysing with 350 cc of water and, after 30', separating of the phases and re-extracting of the organic phase with 50 cc of water was carried out.

The collected aqueous extracts were then treated following the procedures illustrated in the Example 5 starting from the addition of acetic acid to adjust the pH to 5.

34.5 g of acid cefazolin (titre 99.5%, purity 99.5%, K.F. 0.4%, colour=120) were obtained (2 g of solution in 8 cc of a 4.6% $NaHCO_3$ solution, absorption at 420 nm; 1 cm cell).

EXAMPLE 7

Synthesis of 7-amino-3-[(1H-1,2,3-triazol-4-yl)-thiomethyl]-cephalosporanic acid (herebelow identified as 3TR), by the 7-aminoglutaryl-3-[(1H-1,2,3-triazol-4-yl)-thiomethyl]-cefalosporanic acid (herebelow identified as Glutaryl 3TR)

2700 cc of water, 72.6 g of sodium 5-mercapto-triazol (herebelow identified as 5MTNa) and $Na_2CO_3$ till pH=5.5, were charged in a 3 liter flask. The solution was heated to 70° C. and 69.7 g of Glutaryl 7-ACA having a titre of 95.5%, equal to 66.6 activity grams, and $Na_2CO_3$ to adjust back the pH to 5.5, were added at said temperature.

The temperature of 70° C. was maintained for 120' controlling the reaction kinetics which resulted:

| Time (minutes) | Concentration (mg/cc) | |
|---|---|---|
| | Glutaryl 7-ACA | Glutaryl 3TR |
| 0 | 22.0 | 3.7 |
| 30 | 11.6 | 13.3 |
| 60 | 6.1 | 17.7 |
| 90 | 2.3 | 19.4 |
| 120 | 1.0 | 20.2 |

Once the reaction was ended, cooling to 20° C. and the next bioconversion step, following the procedure illustrated in the Example 2, were carried out.

The kinetic data concerning the three cycles are reported in the table:

| CYCLE No. | Time (minutes) | pH | Concentration (mg/cc) | |
|---|---|---|---|---|
| | | | Glutaryl 3TR | 3 TR |
| 1 | 30 | 8.0 | 3.7 | 11.0 |
| 1 | 60 | 8.3 | 0.6 | 13.0 |
| 2 | 30 | 8.0 | 4.4 | 12.7 |
| 2 | 60 | 8.3 | 0.6 | 14.2 |
| 3 | 30 | 8.0 | 5.4 | 12.0 |
| 3 | 60 | 8.3 | 1.2 | 14.7 |

27.1 g of 3TR having a titre of 91.8%, HPLC purity 94.8% and colour 180 (1% solution of 2% $NaHCO_3$; absorption at 420 nm; 1 cm cell) were obtained from the $2^{nd}$ and $3^{rd}$ cycles after precipitation at pH 4.2, filtration and drying.

The loss of 3TR in the mother liquours (2230 cc) was equal to 0.7 mg/ml. The stoichiometric yield from Glutaryl 7-ACA to 3TR was 70%.

$^1$H-NMR (DMSO/DC1) (δ ppm): 3.67–3.73 (Abq, J=18.1 Hz, 2H, —$CH_2$—); 3.91–4.09 (Abq, J=12.9 Hz, 2H, —$CH_2$—); 5.00 (d, J=4.7 Hz, 1H, C-6); 5.20 (d, J=4.7 Hz, 1H, C-7); 8.04 (s, 1H, vinyl H).

EXAMPLE 8

Synthesis of the 7-amino-3-[(1-methyl-1H-tetrazol-5-yl)-thiomethyl]-cephalosporanic acid (herebelow indicated as 3TZ) by the 7-amino-glutaryl-3-[(1-methyl-tetrazol-5-yl)-thiomethyl]-cephalosporanic acid (herebelow indicated as Glutaryl 3TZ)

The Example 7 was reproduced, replacing 5MTNa with 68.5 g of methylmercaptotetrazol (herebelow indicated as MMT) and 48.0 g of $Na_2CO_3$.

Kinetics of the synthesis of Glutaryl 3TZ:

| Time (minutes) | Concentration (mg/cc) | |
|---|---|---|
| | Glutaryl 7-ACA | Glutaryl 3TZ |
| 0 | 19.6 | 5.3 |
| 30 | 8.8 | 15.3 |
| 60 | 4.5 | 17.9 |
| 90 | 1.9 | 19.0 |
| 120 | 1.0 | 18.2 |

3TZ having a titre of 95.5%, HPLC purity of 91.8% and colour 60 (1% solution of 2% $NaHCO_3$; absorption at 420 nm; 1 cm cell) was obtained by subsequent bioconversion, precipitation at pH 4.2, filtration and drying.

$^1$H-NMR (DMSO/DCl) (δ ppm): 3.80–3.86 (Abq, J=17.9 Hz, 2H, —$CH_2$—); 3.98 (s, 3H, —$CH_3$); 4.31–4.46 (Abq, J=13.3 Hz, 2H, —$CH_2$—); 5.13 (d, J=4.9 Hz, 1H, C-6); 5.20 (d, J=4.9 Hz, 1H, C-7).

EXAMPLE 9

Synthesis of the 7-amino-3-[(1,2,5,6-tetrahydro-2-methyl-5,6-dioxo-1,2,4-triazin-3-yl)-thiomethyl]-cephalosporanic acid (herebelow indicated as ACT) by the 7-aminoglutaryl-3 -[(1,2,5,6-tetrahydro-2-methyl-5,6-dioxo-1,2,4-triazin-3-yl)-thiomethyl]-cephalosporanic acid (herebelow indicated as Glutaryl ACT)

The same procedure of the Example 7 was followed replacing 5MTNa with 15 g of thiotriazinone (1,4,5,6-tetrahydro-2-methyl-3-mercapto-5,6-dioxo-1,2,4-triazine) and 13 g of $Na_2CO_3$.

The nucleophilic substitution reaction in position 3 was carried out at pH 6.6 and was characterised by the following kinetic course:

| Time (minutes) | Concentration (mg/cc) | |
| --- | --- | --- |
| | Glutaryl 7-ACA | Glutaryl ACT |
| 0 | 43.9 | — |
| 30 | 20.1 | 34.2 |
| 60 | 7.9 | 43.1 |
| 90 | 4.7 | 46.2 |
| 120 | 2.9 | 46.1 |

ACT having a titre of 91.1%, HPLC purity of 98.4%, was obtained carrying out the bioconversion step on the solution and subsequent precipitation at pH 4.2, filtration and drying.

$^1$H-NMR (D$_2$O/NaHCO$_3$) (δ ppm): 3.45–3.72 (ABq, J=17.8 Hz, 2H, —CH$_2$—); 3.64 (s, 3H, —CH$_3$); 4.04–4.35 (ABq, J=13.4 Hz, 2H, —CH$_2$—); 4.75 (d, J=4.9 Hz, 1H, C-6); 5.04 ppm (d, J=4.9 Hz, 1H, C-7).

We claim:

1. A process for the preparation of a cephalosporin compound which is cefazolin, cefazedone, cefoperazone, cefamandole, cefatrizine or ceftriaxone, which comprises:

reacting glutaryl 7-ACA of the formula:

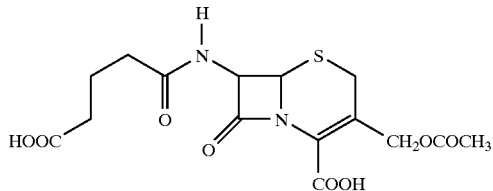

with a compound of formula (II):

R—SH    (II)

wherein R is 5-methyl-1,3,4-thiadiazol-2-yl, 1H-1,2,3-triazol-4-yl, 1-methyl-tetrazol-5-yl or
1,2,5,6-tetrahydro-2-methyl-5,6-dioxo-1,2,4-triazin-3-yl group, in an aqueous solution in an amount of 3–5 mols per mol of glutaryl 7-ACA from about 20° C. to about 90° and for a time from about 2 to about 10 hours;
optionally recovering the excess of the compound of formula (II), thereby preparing a compound of formula (III) in an aqueous solution:

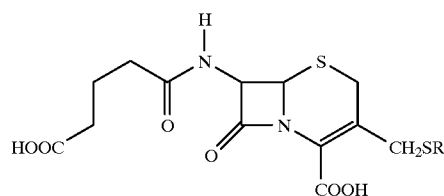

wherein R is as above defined and deacylating said compound of formula (III): and reacting the resulting compound of formula (I)

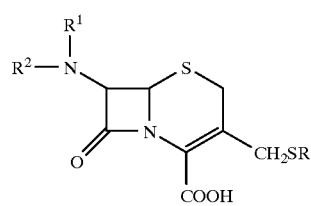

wherein R is as defined above and R$^1$ and R$^2$ are each hydrogen, in the presence of a non-chlorinated solvent, with a mixed anhydride of the necessary acetic acid to form one of said cephalosporins.

2. The process of claim 1, wherein the deacylation step on compound of formula (III) is conducted enzymatically.

3. The process of claim 2, wherein the enzyme of the deacylation of the compound of formula (I) is recovered and optionally reused.

4. A method for the preparation of a pharmaceutical composition comprising cefazolin, cefazedone, cefoperazone, cefamandole, cefatrizine and ceftriaxone, which comprises:

combining the cephalosporin prepared by the process of claim 1 with a pharmaceutically acceptable vehicle or diluent.

* * * * *